US009481865B2

(12) United States Patent
Zhang et al.

(10) Patent No.: US 9,481,865 B2
(45) Date of Patent: Nov. 1, 2016

(54) SERUM-FREE FREEZING MEDIUM USED IN ADIPOSE-DERIVED STEM CELLS AND ESTABLISHMENT OF ADIPOSE-DERIVED STEM CELL LIBRARY

(75) Inventors: Helen Zhang, Shanghai (CN); Luyi Zhang, Jiangsu (CN); Wei Cao, Shanghai (CN)

(73) Assignees: Cellular Biomedicine Group (Shanghai) Ltd, Shanghai (CN); Cellular Biomedicine Group (Wuxi) Ltd, Wuxi, Jiangsu (CN)

( * ) Notice: Subject to any disclaimer, the term of this patent is extended or adjusted under 35 U.S.C. 154(b) by 66 days.

(21) Appl. No.: 14/369,448

(22) PCT Filed: Aug. 6, 2012

(86) PCT No.: PCT/CN2012/079737
§ 371 (c)(1),
(2), (4) Date: Jun. 27, 2014

(87) PCT Pub. No.: WO2013/020492
PCT Pub. Date: Feb. 14, 2013

(65) Prior Publication Data
US 2015/0011429 A1 Jan. 8, 2015

(30) Foreign Application Priority Data
Aug. 9, 2011 (CN) .......................... 2011 1 0227449

(51) Int. Cl.
*C12N 5/071* (2010.01)
*A01N 1/02* (2006.01)
*C12N 5/00* (2006.01)

(52) U.S. Cl.
CPC ............. *C12N 5/0626* (2013.01); *A01N 1/021* (2013.01); *C12N 5/0037* (2013.01); *C12N 2501/999* (2013.01)

(58) Field of Classification Search
CPC ............. C12N 5/0037; C12N 5/0626; C12N 2501/999
USPC ......................................... 506/14
See application file for complete search history.

(56) References Cited

U.S. PATENT DOCUMENTS

2010/0124564 A1* 5/2010 Martinson .............. A61K 35/39
424/424

FOREIGN PATENT DOCUMENTS

CN 102002475 4/2011

OTHER PUBLICATIONS

Hunt et al., Methods in Molecular Biology, vol. 368, Cryopreservation and Freeze Drying Protocols, Second Edition, Chapter 18, Humana Press, 2007, pp. 1-365.*
O.W. Merten et al., "A Simple Serum-free Freezing Medium for Serum-free Cultured Cells," Biologicals, vol. 23 (1995) p. 185-189.
Q. Z. Wang and C. S. Hna, "Serum-free Knockout™SR Medium Supports the Short-time Viability of Mouse Spermatogonial Stem Cells," Journal of Molecular Cell Biology, vol, 41, No. 2 (2008) p. 162-166.
H. Wang et al., "Knockout serum replacement improves establishment efficiency of C57BL/6J mouse embryonic stem cell line," Chin J. Cell Mol Immunol, vol. 23, No. 3 (2007) p. 269-272.
C. Li and Y. Liu, "Modification of in situ cryopreservation of Human Adipose Mesenchymal stem cells," Chinese Journal of Aesthetic Medicine, vol. 16, No. 8 (2007), p. 1026-1028.
International Search Report for international application No. PCT/CN2012/079737, dated Nov. 15, 2012 (2 pages).
K. Zou et al., "Production of offspring from a germline stem cell line derived from neonatal ovaries," Nature Cell Biology, vol. 11, No. 5 (2009), p. 631-636 plus 14 pages of supplementary information.
W. Zhang et al., "The cryopreservation study of adult adipose-derived mesenchymal stem cells," Journal of Lanzhou University (Medical Sciences), vol. 34, No. 2 (2008) 6 pages.

* cited by examiner

*Primary Examiner* — Larry Riggs
*Assistant Examiner* — Karla Dines
(74) *Attorney, Agent, or Firm* — Hamre, Schumann, Mueller & Larson, P.C.

(57) ABSTRACT

Disclosed is a serum-free freezing medium used in adipose-derived stem cells and a method for establishing an adipose-derived stem cell library. The serum-free freezing medium comprises a serum-free culture medium, dimethyl sulfoxide and a serum substitution component KSR; the defects of unstable freezing quality of the adipose-derived stem cells and influence of harmful factors in serum on the adipose-derived stem cells are solved, and the adipose-derived stem cells stored have the advantages of high survival percentage, well adherence growth and strong differentiation capacity.

3 Claims, 3 Drawing Sheets

A

B

Figure 1:
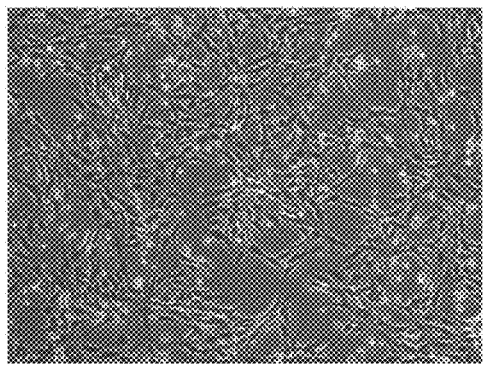
Figure 1:
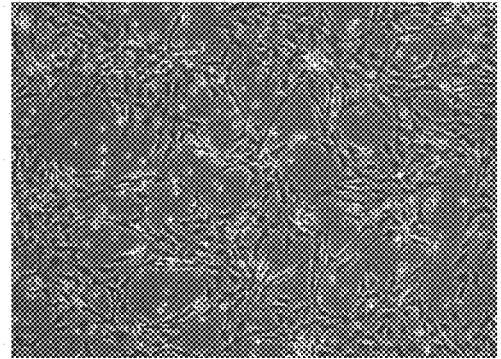

SERUM-FREE FREEZING MEDIUM USED IN ADIPOSE-DERIVED STEM CELLS AND ESTABLISHMENT OF ADIPOSE-DERIVED STEM CELL LIBRARY

FIELD OF INVENTION

The present invention relates to the field of biotechnology and, in particular, to the serum-free freezing medium for adipose-derived stem cells and establishment of adipose-derived stem cell library.

BACKGROUND OF THE INVENTION

Stem cell (SC) is a type of pluripotent cells of self-replicating ability which can differentiate into various types of functional cells. Nowadays, mesenchymal stem cell is one type of adult stem cells, which has pluripotent self-replicating ability and has attracted much attention. Mesenchymal stem cell can be cultured and amplified in vitro, and can differentiate into several tissue cells such as bone cells, cartilage cells, fat cells, nerve cells, muscle cells and so on.

In recent years, bone marrow stem cells, umbilical cord stem cells and adipose-derived stem cells (ADSCs) are studied intensively. Adipose-derived stem cell is one type of stem cells having pluripotent self-replicating ability and isolated from adipose tissue. ADSCs have several advantages over bone marrow stem cells and umbilical cord stem cells. It has been found in the research that ADSCs can proliferate in vitro steadily with low decline rate, while it is easy to obtain sources for ADSCs and a large amount of ADSCs can be obtained from a small amount of tissue. ADSCs are appropriate for large-scale culture and grow homogenously while damage to body is small. Moreover, ADSCs have wide resources and large amount of storage in body and ADSCs are appropriate for autoplastic transplantation, and highly safe. The establishment of adipose-derived stem cell library has become a new focus in recent years.

Since the isolation and culturing of human adipose-derived mesenchymal stem cells need a long period, it takes about two weeks or more for primary cells to grow to confluence, and about three weeks to reach certain amount of cells. Long term in vitro cultivation and passage of human adipose-derived mesenchymal stem cells usually leads to a spontaneous differentiation, which results in losing of multi-differentiation potential. Therefore, in order to ensure the continuity of the experiment, it is necessary to provide seed cells in large amounts for experiments or tissue engineering at any time. Therefore, it is necessary to establish an effective method of cryopreservation. The reliability of cryopreservation methods is identified by detecting cell cycle, cell phenotype and adipogenic differentiation potential of human adipose-derived mesenchymal stem cells after cryopreservation and recovery.

At present, the cryopreservation usually adopts serum for cryopreservation. Serum is the greatest used natural medium in cell culture, and its main advantages are as follows:

(1) It contains plenty of nutrients necessary for cell growth so as to sufficiently support cell growth.

(2) The plenty of serum proteins play a protective role on cells.

(3) Growth factors and trace elements essential for cell proliferation are provided for in vitro cell culture;

(4) It provides adherence factors for adherence-dependent cells.

However, there are various disadvantages in using animal serum in freezing medium, mainly including:

(1) Serum contains substances which are toxic for cells, such as polyamine oxidase which can react with polyamines (e.g., spermine, spermidine) from highly reproductive cells, thus forming polyspermine which is cytotoxic. Complement, antibodies and bacteria toxins affect cell growth, and even cause cell death;

(2) Depending on individual animal, origin of serum, and batch number of serum, the quality of each batch of serum varies greatly and it is possible to maintain the consistency of composition.

(3) During the collecting of materials, mycoplasma and viruses may be bought into the serum and cause potential effects on cells, resulting in failure of experiments or unreliable experimental results.

(4) The cost of serum is quite expensive and up to 3000-4000 RMB per 500 ml of serum.

(5) Acquisition of serum from a living body is harmful to animal.

So far, there is no serum-free freezing medium which strictly suitable for adipose-derived stem cells or establishment of adipose-derived stem cell library. Therefore, it is urgent need in the art to develop a new and effective serum-free freezing medium suitable for adipose-derived stem cells.

SUMMARY OF INVENTION

One object of the present invention is to provide an efficient serum-free freezing medium for adipose-derived stem cells and a use thereof, thus avoiding the possible risks of freezing medium containing serum in clinical use.

Another object of the present invention is to provide a new type of adipose-derived stem cell library of high efficiency and the establishment method thereof.

In the first aspect of the present invention, it provides a serum-free freezing medium, wherein it comprises the following ingredients: serum-free culture medium, dimethylsulfoxide (DMSO) and serum substitute Knockout™ Serum Replacement (KSR), and the freezing medium does not contain any serum.

In a preferred embodiment, based on the volume of serum-free freezing medium, the content of serum-free culture medium is a and a is from 5%-15% (v/v), the content of DMSO is b and b is from 8%-20% (v/v), and the content of KSR is c and c is from 70%-85% (v/v), while a+b+c100%.

In a preferred embodiment, a is from 8%-12% (v/v), b is from 10%-14% (v/v), and c is from 75%-80% (v/v), by volume.

In a preferred embodiment, a is 10% (v/v), b is 12% (v/v), and c is 78% (v/v), by volume.

In a preferred embodiment, the serum-free culture medium is selected from the group consisting of DEME culture medium and UltraMEM culture medium.

In a preferred embodiment, the serum-free culture medium is commercially available DEME culture medium, which comprises appropriate amount of insulin, transferrin, penicillin and streptomycin.

In the second aspect of the present invention, it provides a use of the serum-free freezing medium of the first aspect of the present invention for long-term storage of adipose-derived stem cells and/or establishment of an adipose-derived stem cell library.

In the third aspect of the present invention, it provides an adipose-derived stem cells mixture, wherein the mixture comprises:

adipose-derived stem cells, and the serum-free freezing medium of the first aspect of the present invention.

In the fourth aspect of the present invention, it provides an adipose-derived stem cell library, wherein the library comprises the adipose-derived stem cells mixture of the fourth aspect of the present invention.

In a preferred embodiment, the mixture of the adipose-derived stem cells and serum-free freezing medium is preserved in liquid nitrogen after it is cooled in a programmed gradient cooling.

In a preferred embodiment, after recovery, the recovered adipose-derived stem cells of the library have an ability of adipogenic induction.

In a preferred embodiment, the survival rate of the recovered adipose-derived stem cells of the library is ≥90%.

In a preferred embodiment, the survival rate of the recovered adipose-derived stem cells of the library is ≥95%.

In the fifth aspect of the present invention, it provides a use of the adipose-derived stem cell library of the fourth aspect of the present invention for long-term preservation of adipose-derived stem cells.

In the sixth aspect of the present invention, it provides a method for establishing an adipose-derived stem cell library, wherein it comprises:

(i) washing an adipose tissue material containing adipose-derived stem cells, thereby obtaining a tissue mixture from which blood cells are removed;

(ii) digesting the tissue mixture obtained in step (i), thereby obtaining a digested adipose tissue mixture;

(iii) filtrating the digested adipose tissue mixture obtained in the former step to remove undigested tissue pieces, thereby obtaining a filtrate comprising adipose-derived stem cells;

(iv) centrifuging the filtrate obtained in the former step, and discarding fat in upper layer, thereby obtaining a precipitate which contains adipose-derived stem cells;

(v) inoculating and passaging the adipose-derived stem cells obtained in step (iv), thereby obtaining adipose-derived mesenchymal stem cells;

(vi) digesting the adipose-derived mesenchymal stem cells, thereby obtaining dispersed adipose-derived stem cells;

(vii) mixing the adipose-derived stem cells obtained in step (vi) with the serum-free freezing medium of the first aspect of the present invention, and preserving the mixture under low temperature, thereby obtaining the adipose-derived stem cell library.

In a preferred embodiment, the digestion of step (ii) comprises collagenase digestion, preferably collagenase I digestion.

In a preferred embodiment, the digestion of step (vi) comprises trypsin digestion.

In a preferred embodiment, the step (vii) comprises: mixing the serum-free freezing medium with the adipose-derived stem cells obtained in step (vi) so as to form an adipose-derived stem cells mixture, and the mixture is cooled and preserved in liquid nitrogen, thereby obtaining the adipose-derived stem cell library.

In a preferred embodiment, the cooling of step (vii) comprises using a programmed freezing method for gradient cooling; preferably the cooling rate is −1° C./min to −2° C./min.

In a preferred embodiment, when the temperature reaches below −25° C. in step (vii), the cooling rate is adjusted to −5° C./min to −10° C./min.

In a preferred embodiment, when the temperature reaches −100° C. in step (vii), the adipose-derived stem cells is preserved in liquid nitrogen directly.

In the seventh aspect of the present invention, it provides an autograft composition, which comprises:

an effective amount of adipose-derived stem cells which are recovered after preserved with the serum-free freezing medium of the first aspect of the present invention, or adipose-derived stem cells which are recovered from the adipose-derived stem cell library of the fourth aspect of the present invention, and at least one pharmaceutically acceptable carrier or diluent.

It should be understood that, in the present invention, the technical features specifically described above and below (such as in the Examples) can be combined with each other, thereby constituting one or more new or preferred technical solutions which are not specifically described one by one because of the limitation of context.

DESCRIPTION OF FIGURES OF THE INVENTION

FIG. 1 shows the recovery results of adipose-derived stem cells treated with an ordinary freezing medium which contained serum and the serum-free freezing medium of the present invention; wherein FIG. 1A shows the recovery results of adipose-derived stem cells in the group which were treated with an ordinary freezing medium which contained serum; and FIG. 1B shows the recovery result of adipose-derived stem cells in the group which were treated with the serum-free freezing medium of the present invention.

Figure 2:
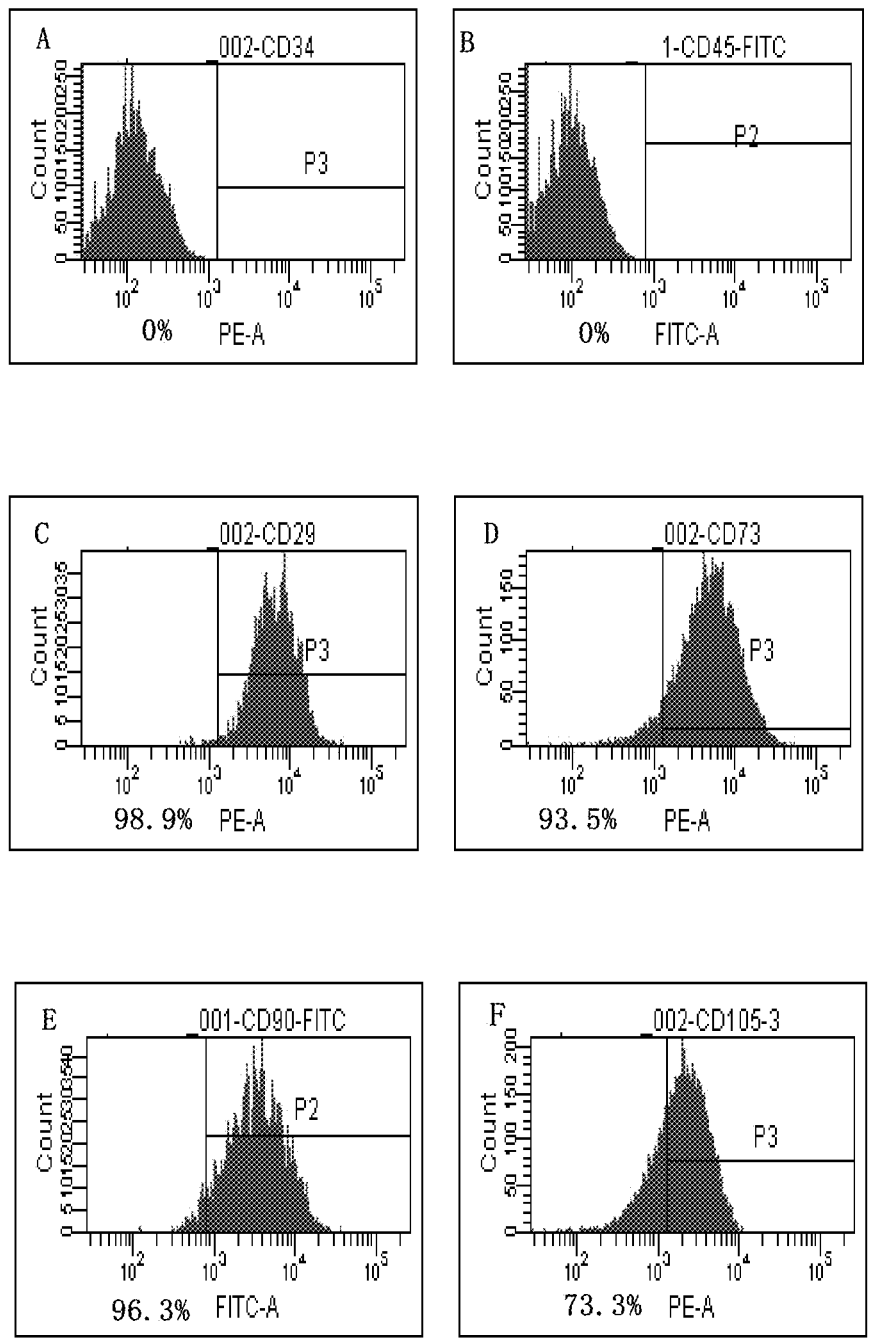

FIG. 2 shows the identification results of surface markers of antigen protein identified by flow cytometry on adipose tissue-derived stromal cells which were recovered after cryopreserved in the serum-free freezing medium of the present invention (the formulation was shown in Example 3). The results indicated that the purity of the adipose-derived stem cells was quite high. FIG. 2A shows that the rate of the recovered adipose-derived stem cells containing CD34 was 0%. FIG. 2B shows that the rate of the recovered adipose-derived stem cells containing CD45 was 0%. FIG. 2C shows that the rate of the recovered adipose-derived stem cells containing CD29 was 98.9%. FIG. 2D shows that the rate of the recovered adipose-derived stem cells containing CD73 is 93.5%. FIG. 2E shows that the rate of the recovered adipose-derived stem cells containing CD90 is 96.3%. FIG. 2F shows that the rate of the recovered adipose-derived stem cells containing CD105 is 73.3%.

Figure 3:
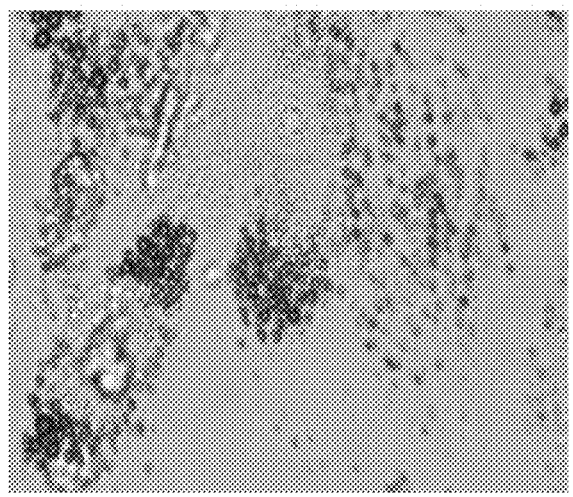
Figure 3:
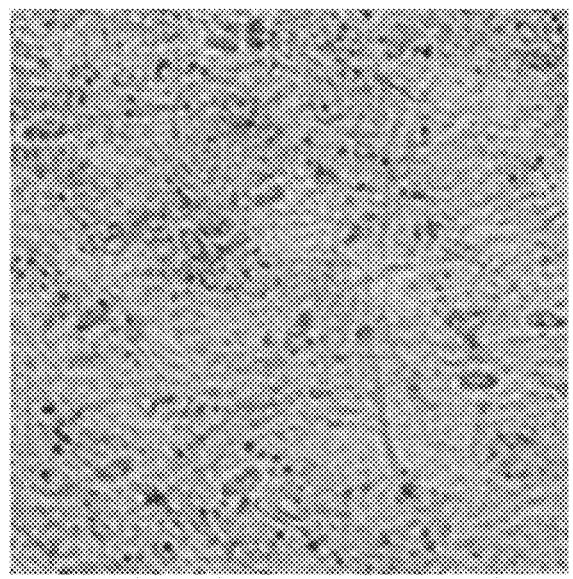

FIG. 3 shows the adipogenic induction results of the adipose-derived stem cells which were recovered after cryopreservation in the serum-free freezing medium of the present invention (the formulation was shown in example 3). FIG. 3A shows induction results of the recovered adipose-derived stem cells in an adipogenic induction medium. The results shows that the adipose-derived stem cells treated with the serum-free freezing medium of the present invention (the formulation was shown in Example 3) have a strong adipogenic ability after recovery. FIG. 3B shows that the recovered adipose-derived stem cells did not posses adipogenic ability when ADSCs were cultured in normal culture medium.

DETAILED DESCRIPTION OF THE INVENTION

Through comprehensive and intensive research, the inventor has unexpectedly discovered that although most substitute of serum cannot be used to replace serum in freezing medium, one specific serum-free freezing medium prepared by KSR can provide cryopreservation effect dramatically superior to freezing medium containing serum, thus providing a new serum-free freezing medium suitable for long term preservation of adipose-derived stem cells for the first time. The freezing medium of the present invention has overcome the demerits of the traditional freezing medium. The adipose-derived stem cells from an adipose-derived stem cell library established with the freezing medium of the present invention are well preserved and of strong differentiation potency. The present invention is accomplished based on the discovery.

Terms

As used herein, the terms "more than" and "less than", include the number itself, for example, "more than 95%" means ≥95%, "less than 0.2%" means ≤0.2%.

The terms "serum-free" or "substantially free of serum" can be used interchangeably, which mean that serum component is ≤0.1%, preferably ≤0.01%, more preferably ≤0.005% (such as 0%), based on the total weight of the freezing medium.

Adipose-Derived Stem Cells (ADSCs)

As used herein, the term "adipose-derived stem cells" refers to stem cells that are separated from adipose tissue. Specifically, adipose-derived stem cells are stem cells separated from adipose tissue and possess multiple differentiations potential. There is no particular limitation on the adipose tissues or the adipose materials in the present invention, which can be from any adipose tissues of any position of animal or human, preferably human adipose tissues. Preferably, adipose tissues are tissues from positions such as waist, hips, abdomen, thighs, upper arms, etc. ADSCs can proliferate steadily in vitro with low decline rate. ADSCs are easy to obtain raw materials, in a large amount of storage in body, suitable for cultivation in large-scale and with a minimum body harm. Further, ADSCs have extensive sources and are suitable for autotransplantation.

Serum-Free Medium

As used herein, the term "serum-free medium" refers to medium which is substantially free of serum and which can maintain in vitro growth and proliferation of cells for a long period. There is no particular limitation on the serum-free medium of the present invention, which can be any serum-free culture medium suitable for cultivation or preservation of stem cells (in particular ADSCs).

In general, the basic components of serum-free medium include, but are not limited to:

Inorganic salts. The inorganic salts can regulate the intracellular osmotic pressure, adjust the enzyme activity and the pH value of solution; generally, the inorganic salts include $CaCl_2$, $KCl$, $MgSO_4$, $NaCl$, $NaHCO_3$, $NaH_2PO_4$, etc.

Amino acids. The amino acids are the indispensable materials for protein synthesis of cells. Generally, the amino acids include valine, leucine, isoleucine, threonine, lysine, tryptophan, phenylalanine, methionine, histidine, tyrosine, arginine and cysteine, etc.

Vitamins. Vitamins are biologically active substances which maintain cells by forming a cofactor or coenzyme. Usually, fat-soluble vitamins include VA, VD, VE and VK, etc. Generally, the water-soluble vitamins include folic acid, nicotinamide, pantothenic acid, pyridoxine, riboflavin and thiamine, etc.

Carbohydrates. Carbohydrates are energy source of cells, and also the components for nucleic acids and proteins. Glucose is the most important carbohydrate component.

Trace elements. Trace elements are important components which promote cell growth and activate the function of zymoprotein. Selenium is the most common trace element.

Growth factors and hormones. Different growth factors and hormones such as insulin can be added into for different cells.

Adherence promoting materials. Many cells must grow in adherence condition, and adherence promoting materials usually are extracellular matrix materials, such as fibronectin, laminin, and the like.

Serum-free medium may also comprise antibiotics. The common antibiotics include but are not limited to penicillin, streptomycin and the final concentration of antibiotics is generally 20-100 mg/ml, and preferably 50 mg/ml.

One skilled in the art can formulate serum-free culture medium by using conventional methods, or can purchase various commercially available serum-free medium, including (but not limited to): DEME serum-free culture medium, UltraMEM serum-free culture medium and so on.

Dimethyl Sulfoxide (DMSO)

The dimethyl sulfoxide is a sulfur-containing organic compound which is colorless and odorless and transparent liquid under room temperature. It has features such as high polarity, high boiling point, good thermal stability, non-proton, miscible with water, and can be dissolved in ethanol, propanol, benzene and chloroform and in most organic substances. In cell culture, DMSO can act as a protective agent of permeability, and it can reduce the freezing point of cells, reduce the formation of ice crystals, reduce the damage of free radical to cells, and change the permeability of biofilm to electrolyte, drugs, toxins and metabolites.

Serum-Free Freezing Medium

The present invention provides an effective serum-free freezing medium suitable for adipose-derived stem cells, which comprises:

serum-free medium, dimethyl sulfoxide (DMSO) and serum substitute Knockout™ Serum Replacement (KSR), and the freezing medium does not contain any serum.

Generally, the content of serum-free culture medium is 5%-15%, the content of DMSO is 8%-20%, and the content of KSR is 70%-85%, by volume. Preferably, the content of serum-free culture medium is 8%-12%, the content of DMSO is 10%-14%, and the content of KSR is 75%-80%. More preferably, the content of serum-free culture medium is 10%, the content of DMSO is 12%, and the content of KSR is 78%.

Cell Cryopreservation

Cell cryopreservation technique is an important method for preserving species in biological sciences. If the cryopreservation is conducted without any additional conditions, water of intracellular and extracellular environment forms ice crystals, which lead to mechanical damages, increases of electrolyte level, changes of osmotic pressure, dehydration, PH change, and protein denaturation in cells, and even lead to cell death. The freezing point will drop as far as a protecting agent is added into the culture medium. It makes intracellular water to permeate out of cells before frozen under slow freezing conditions. The formulation of ice crystals is reduced if stored at a low temperature below −130° C.

The freezing medium is the most important part for cryopreservation. The traditional freezing medium contains animal serum, mainly fetal calf serum and/or bovine calf serum. Serum is a sort of extremely complex mixtures which are produced by removing fibrin from plasma. Some of the constituents of serum are still unclear. Moreover, the constitutes and contents of the serum vary, depending on sex, age, physiological condition and nutritional conditions of animal donor. Serum comprises various plasma proteins, peptides, fats, carbohydrates, hormones, and inorganics, etc.

The present invention uses a serum-free freezing medium comprising a serum-free medium and a serum substitutes for cell cryopreservation so as to reduce the defects brought by serum of animal cells as well as to ensure the cryopreservation and recovery effects of cells.

Cell cryopreservation can be conducted by conventional equipments and methods. In a preferred embodiment, a programmed cooling is used. The cooling box is typically made of polycarbonate, high density polyethylene or foam. Moreover, isopropanol and mechanical refrigeration system are required. The cooling rate is adjustable and repeatable so as to meet requirements on cell cryopreservation and recovery. A typical cooling procedure comprises: cooling with a cooling rate of −1 to −2° C./min; when the temperature reaches lower than −25° C., adjusting cooling rate into −5 to −10° C./min; and quickly immersing into liquid nitrogen when the temperature reaches lower than −100° C. The cells can be preserved in liquid nitrogen for a long period, which can be decades of years or more.

Cell Library

As used herein, the term "cell library" refers to a population of cells which are cooled using a certain program and are long-term preserved in specific freezing medium. The cells of cell library can be from human source or (non-human) mammal sources such as rats, mice, monkeys, cats, sheep, etc.; and from poultry sources, such as chickens. Cells can be from different organs or tissues, such as: oral cavity, kidney, liver, lymph, muscle, ovary. Cells from cell library can be preserved for decades of years or more.

Recovery of Cells

As used herein, the term "recovery of cells" refers to the process in which the cells are re-activated from dormant state. Generally, rapid recovery, a procedure known by the skilled in the art, is used in the recovery of cells, which comprises quickly shifting the freezing tube from liquid nitrogen into warm water bath of which the temperature is preferably 37° C.-40° C.; stirring in variable interval to speed up unfreezing; sterilizing the freezing tube after the cells are completely unfrozen; washing and re-suspending the unfrozen cells, transferring the cells into cell culture flask and cultivating in $CO_2$ incubator; and determining the survival rate and viability of cells.

Cell Adherence

As used herein, the term "cell adherence" refers to the fact that there is a supporting surface for attachment during the growth of normal cells, while cells grow and proliferate on the surface by the adherent factors excreted by themselves or provided in the medium. The cells format into two forms after growth on the surface, which are fibroblast-like cell or epithelioid cells. There is a contact inhibition phenomenon during adherent growth. Trypsin treatment is conducted during culture of animal cells to make the adherent cells fall off. Meanwhile, the tumor cells do not have these features and can be cultivated in suspension cultivation.

Detection of Stem Cell Antigen

The adipose-derived stem cells cryopreserved by the method of the present invention are of high purity after recovery, which is proven by detecting cell surface antigens.

There are several specific antigens and receptors of the adipose-derived stem cells, mainly CD3, CD13, D29, CD34, CD45, CD49e, CD59, CD73, CD90, CD105, HLA-ABC, etc.

CD34 antigen is a highly glycosylated type I transmembrane protein which selectively expresses on surface of human hematopoietic stem cells (HSC), progenitor cells (PC) and vascular endothelial cell (EC). The ratio of adipose-derived stem cells with CD34 in stem cells is preferably ≤0.2%, more preferably, ≤0.2%.

CD45 exists on the surface of every hematopoietic stem cell, including hematopoietic stem cell and osteoclast, the ratio of adipose-derived stem cells with CD45 in stem cells is preferably ≤0.1%.

CD29, CD73, CD90, and CD105 etc mainly exist on the surface of adipose tissue-derived stromal cells.

The ratio of adipose-derived stem cells with CD29 in stem cells is preferably ≥95%, more preferably ≥97%, most preferably ≥98%.

The ratio of adipose-derived stem cells with CD73 in stem cells is preferably ≥80%, more preferably ≥90%, most preferably ≥93%.

The ratio of adipose-derived stem cells with CD90 in stem cells is preferably ≥80%, more preferably ≥90%, most preferably ≥95%.

The ratio of adipose-derived stem cells with CD105 in stem cells is preferably ≥70%, more preferably ≥72%, most preferably ≥75%. The skilled in the art can use common methods to detect purity and differentiation degree of adipose-derived stem cells, such as flow cytometry method. Different specific targeting antibodies are added during detection, wherein the antibodies may be intact monoclonal or polyclonal antibodies, or the antibodies may be antibody fragment of immunoreactive, such as Fab' or $(Fab)_2$ fragment; heavy chain of antibody; light chain of antibody; single chain Fv molecule which is genetically engineered (Ladner et al, U.S. Pat. No. 4,946,778); or chimeric antibodies such as antibodies which have murine antibody binding specificity while still retain part of human antibody. The cells are automatic analyzed and sorted by flow cytometry after antibodies are added and bind onto antigen on cell surface for a certain period of time.

Adipogenic and Testing

Since the adipose-derived stem cells have a multi-directional differentiation capacity, certain differentiated cells having a particular function can be obtained by differentiation inducing adipose-derived stem cells under certain conditions.

The adipogenic induction of adipose-derived stem cells can be conducted by skilled in the art with any common methods. One preferred induction method is to add dexamethasone into the culture medium. There are mainly 3 types of induction medium containing dexamethasone: 1. dexamethasone+1-methyl-3-isobutylxanthine (IBMX), 2. dexamethasone+insulin, 3. dexamethasone+indomethacin, 1-methyl-3-isobutylxanthine and insulin. The most important substance of the induction medium is dexamethasone. Low concentration of dexamethasone is one of the essential components of cultivation of mesenchymal stem cells with low serum or serum-free culture, which can promote in vitro rapid proliferation of mesenchymal stem cells; while higher concentration of dexamethasone can induce mesenchymal stem cells differentiate into adipocytes.

The skilled in the art can use common methods and stains (e.g. Oil Red, Sudan Red 5B, and Solvent Red 27, etc.) to detect the adipogenic induction of stem cells. One preferred stain is Oil Red (O), i.e., Oil Red O. Structure of Oil Red O is 1-2,5-dimethyl-4-(2,5-dimethylphenylazo)phenylazo-2-naphthol, which is a red powder. It is an oil-soluble azo dyes, easily soluble in benzene, ethanol and acetone. During the adipogenic induction, the oil droplets constantly accumulate in the cytoplasm of cells, and continuously increase in volume, and eventually, the oil droplets occupy the cytoplasm. As a biological stain, Oil Red O is easy to combine with oil, but of poor tinting strength to the structure of the cells themselves. Adipogenic staining observation can be clearly conducted by using a microscope.

Autotransplantation Composition and Administration Thereof

The present invention further provides an autotransplantation composition which is useful for multiple purposes such as anti-aging. Autotransplantation composition comprises an effective dose of adipose-derived stem cells which are recovered after preserved with the serum-free freezing medium of the present invention. In a preferred embodiment, it can further comprise at least one pharmaceutically acceptable carrier or diluent. The active ingredient is usually mixed with an excipient or is diluted with an excipient when preparing the composition. For compositions containing adipose-derived stem cells, the preferred formulation is liquid formulations.

The prepared autotransplantation composition can be administrated or applied via common route of administration, comprising (but not limited to): intramuscular, intraperitoneal, intravenous, subcutaneous, intradermal, or topical administration.

When using the autotransplantation composition of the present invention, a safe and effective dose is administrated to human, wherein the safe and effective dose is usually $10^5$-$10^8$ cells/person/once, preferably $10^6$-$10^7$ cells/person/once. Of course, the specific dose should vary according to factors such as way of administration and health condition of the subject, which is within the ability scope of skilled physician.

The main advantages of the serum-free freezing medium of the present invention include:

(1) The medium has clear ingredients and does not contain any ingredients harmful to cells.

(2) The medium has a stable quality and the contents of nutrition ingredients would not vary with batches.

(3) The cells can be well recovered after cryopreservation with a high survival rate;

(4) The cells after cryopreservation have a stable antigenic characteristics and a high purity.

(5) The recovered adipose-derived stem cells have strong differentiation ability after preservation.

The present invention will be further illustrated below with reference to the specific examples. It should be understood that these examples are only to illustrate the invention but not to limit the scope of the invention. The experimental methods with no specific conditions described in the following examples are generally performed under the conventional conditions, e.g., in the conditions described in Sambrook et al, Molecular Cloning: A Laboratory Manual (New York: Cold Spring Harbor Laboratory Press, 1989), or according to the manufacturer's instructions. Unless indicated otherwise, parts and percentage are calculated by weight.

Example 1

The separation of adipose-derived stem cells
1. Reagents and Consumables
Sterile skillet forceps
Sterile filter
50 ml centrifugal tubes
Culture flasks
DMEM serum-free medium (purchased from Hyclone Company)
0.125% Trypsin—0.01% EDTA solution
The preparation method of 0.1% collagenase I (freshly prepared): 0.1 g weighed collagenase I powder was dissolved in 100 ml medium without any factors, and pre-heated up to 37° C. before use.

2. The Separation of the Adipose-Derived Stem Cells 2.1. The washing of the adipose tissue (in order to remove blood cells): equal amount of saline was added to a centrifugal tube containing adipose. The lid of the centrifugal tube was tightened, shaken for 3 mins to thoroughly wash the adipose tissue, then stood for 3-5 min to separate the different phases. The lower aqueous phase was removed. The above-mentioned protocol was repeated for three times until the lower layer liquid became relatively clearer.

2.2. The digestion of the Collagenase: After removing the saline, the pre-heated DMEM containing 0.1% collagenase I with equal volume to adipose was added into the centrifugal tube and placed in the shaker at the constant temperature of 37° C., 200 rpm, digested for 1 h. The centrifugal tube was shaken for 5-10 seconds every 15 min (to make the collagenase I and adipose fully contact);

2.3. The collection of the sediment: after digestion, the tube was centrifuged for 10 min at 2000 rpm. The digested adipose in the upper layer was removed and the sediment in the bottom layer of the two tubes is collected into a new centrifugal tube, 50 ml DMEM was then added, centrifuged at 1000 rpm for 8 min, and washed once.

2.4. The filtration and counting: DMEM was added up to 50 ml, mixed and filtered by 100 um filter to remove the undigested tissues. Adding DMEM up to 50 ml, and drawing 1 ml of the mixture from the tube to count the quantity and viability of cells.

Example 2

The Cultivation of the Adipose-Derived Stem Cells

1. Inoculation: the separated adipose-derived stem cells described in Example 1 were centrifuged for 8 min at 1000 rpm, washed once, and inoculated to T75 culture bottle, wherein the inoculum density was adjusted according to the quantity of cells counted (the inoculum density: usually 12 ml of liposuction adipose was inoculated into each T75 culture bottle, i.e., cells separated from the 50 ml of liposuction adipose were inoculated into four T75 culture bottles), then cultured at 37° C. with 5% $CO_2$.

2. Passaging of the cells: the cells became adherent for about 1-2 days after inoculated, among which small amount of adherent mesenchymal stem cells appeared after three days. After cultured for 5-7 days, the adherent cells became colony. Digesting and passaging of the cells were conducted with 0.125% trypsin—0.01% EDTA solution. 2 ml of digestion was added into each T75 culture bottle, and the digestion time was 1.5-2.5 min. Cells were collected and counted, and then digested and passaged by $5\times10^3$/cm² (i.e., 1:1-2 based on the primary adherent situation). The cells became grow faster after passaged, usually it took them three days to passage again. The cells are passaged according to the proportion of 1:2-3 based on the growth condition of the cells. Usually the number of P2 adipose-derived mesenchymal stem cells is more than $2\times10^7$.

Example 3

Cryopreservation of the Cells
1. Reagents and Consumables
2 ml freezing tube
5 ml pipette
10 ml pipette
50 ml centrifugal tube
3 ml plastic straw
40 nm cell filter
Nalgene programmed freezing box (Commercially available Item No. 5100-0001c)
0.25% pancreatin-EDTA
DMSO
serum-free medium (purchased from ScienCell, the Item No. is 7511): The commercially available serum-free medium is DMEM culture medium, which contains appropriate amount of insulin, transferrin, penicillin and streptomycin.
Serum alternatives: Knockout™ Serum Replacement (KSR), (purchased from Invitrogen, Item No. 10828028)
Serum-free freezing medium: 10% serum-free medium+ 12% DMSO+78% serum alternative KSR by volume;
Ordinary freezing medium: 10% fetal calf serum+10% DMSO+80% DMEM by volume.

2. Cryopreservation 2.1 The morphology of the cells to be cryopreserved was observed, and the cells were digested when their confluency reached 85%-90%.

2.2 Appropriate amount of serum-free medium(2-3 ml/75 cm$^2$) was added into each cultural vessel after cell digestion. The vessels were repeatedly pipetted or shaken until the majority of the cells were dropped off, then moved into a 50 ml centrifugal tube. 4-5 ml PBS was added into the original cultural vessels to wash the wall of vessels, and the washing solution was combined and added into centrifugal tube, centrifuged for 10 min.

2.3 Washing of cells: The supernatant in the centrifuge tube was removed and 2-4 ml PBS was added into each centrifugal tube, and gently pipetted to uniform. The cell suspension of the 15-20 centrifugal tubes were combined into one centrifuge tube, and centrifuged at 210 g for 10 min for washing.

2.4 The serum-free cell freezing medium was gradually added into the cell suspension along the inside wall of the tube, and was pipetted to uniform (the range of the cryopreservation density was 0.5-2×10$^7$/ml), whereas the ordinary freezing medium containing serum was added into the other group. There are five samples for each group.

2.5 Cells to be cryopreserved were placed in the programmed cooling box containing isopropyl alcohol. The amount and the times of usage of the isopropanol must be considered before being used in order to add or replace the isopropanol in time according to protocols. The cells were kept at −80 ° C. overnight in the freezer with the cooling rate of the cooling box kept at −1° C./min, moved into liquid nitrogen tank the next day, by which the bank of adipose stem cell was established.

Example 4

Recovery of the Cells
1. Reagents and Consumables
5 ml pipette
10 ml pipette
3 ml plastic straw
50 ml centrifugal tube
4° C. pre-cooled PBS solution
75% ethanol
2. Recovery 2.1 The temperature of thermostatic water bath was adjusted to 40° C. The cell freezing tube was taken out from the liquid nitrogen, then immediately put into 40° C. warm water and gently shaken until the freezing medium was completely thawed;

2.2 The cap of the freezing tube was wiped with 75% ethanol and burned with flame. The cap of the freezing tube was opened and the cell suspension was transferred into a 50 ml centrifuge tube (it should be noted that the movement should be gentle). 1 ml of 4° C. pre-cooled PBS was then added into the freezing tube, pipetted to wash. The residual cells in the tube were transferred into 50 ml centrifuge tube as much as possible, then mixed by gently pipetting;

2.3 The above-mentioned protocols were repeated. Combining the cell suspension and the washing liquid of the 2-3 freezing tube into one 50 ml centrifugal tube. 4° C. pre-cooled PBS was added into the centrifugal tube (wherein the adding proportion was 10-15 ml per freezing tube). The tube was centrifuged at 210 g for 8 min. The supernatant was removed; and the cells from 2-3 centrifugal tubes could be combined into one 50 ml centrifugal tube, followed by diluting the cells through gradually adding the 4° C. pre-cooled PBS to 45 ml (or dilute by a ratio of 15-20 ml per centrifugal tube), and then gently pipetting to uniform. 10 µl of sample was taken for counting the number and the viability of the cells, and then centrifuged at 210 g for 10 min. The recovered cell population was obtained from the resulting sediment.

Example 5

The Determination of the Recovered Cell Viability of Adipose-Derived Stem Cells

The third generation of the adipose-derived stem cells were cryopreserved by using the serum-free freezing medium described in Example 3. The cell recovery process was proceeded one month later. Five groups were divided and prepared into single-cell suspension of which the concentration was 1×10$^5$ /mL, from which 9 drops were taken and moved into EP tube. One drop of trypan blue solution of which the concentration is 0.4% was added into each tube. Blood counting chamber was used to count the number and the viability of the cells in 2 min. The control group was the recovered cells cryopreserved with ordinary freezing medium and treated by the same method mentioned above.

The results are shown in table 1.

TABLE 1

| | The Cell Viability After Recovery | |
| --- | --- | --- |
| Groups | Ordinary freezing medium containing serum | Serum-free freezing medium of the present invention |
| 1 | 89.0% | 95.5% |
| 2 | 90.5% | 93.5% |

TABLE 1-continued

The Cell Viability After Recovery

| Groups | Ordinary freezing medium containing serum | Serum-free freezing medium of the present invention |
|---|---|---|
| 3 | 91.0% | 94.5% |
| 4 | 93.5% | 95.5% |
| 5 | 96% | 95.0% |
| Average | 92% | 94.8% |

It can be seen from Table 1 that the average cell viability of the cells recovered after cryopreserved with serum-free freezing medium of the present invention is 94.8%, whereas the average cell viability of the cells recovered after cryopreserved with ordinary freezing medium containing serum is 92%. This indicates that the effect of serum-free freezing medium of the present invention is better than that of the control group.

Example 6

The Determination of Cryopreservation Time of the Serum-Free Cryopreservation Solution of the Present Invention In order to determine the cryopreservation effect of the cell bank prepared with the serum-free freezing medium of the present invention (of which the formula is shown in Example 3), the inventor recovered the adipose-derived stem cells which were cryopreserved for 1 month, 3 months and 6 months, respectively. Five samples from each group were stained for counting by the method described in Example 4. The results are shown in table 2.

TABLE 2

| Groups | Recovered after 1 month of cryopreservation | Recovered after 3 months of cryopreservation | Recovered after 6 months of cryopreservation |
|---|---|---|---|
| 1 | 94.5% | 95.5% | 91.0% |
| 2 | 93.5% | 93.0% | 96.5% |
| 3 | 95.0% | 92.5% | 95.0% |
| 4 | 94.5% | 94.5% | 93.5% |
| 5 | 95.0% | 96.5% | 95.5% |
| Average | 94.5% | 94.4% | 94.3% |

The result showed that the average cell viability of cells cryopreserved for 1 month, 3 months and 6 months were: 94.5%, 94.4%, and 94.3%, respectively, and the recovery condition of cells was fine, which means that the property of cell bank was stable.

Example 7

The Determination of the Adherence Rate of Cells

The cells treated with the serum-free freezing medium of the present invention (of which the formula was shown in Example 3) and the cells treated with the control freezing medium were inoculated separately in 24-well plates with $5 \times 10^4$ cells per well. Each group was inoculated with cells in 3 wells and cultivated for one day. The adherent situation of cells was then observed.

The result is shown in FIG. 1. FIG. 1A shows the adherent situation of the group treated with serum-free freezing medium of the present invention after recovery, and FIG. 1B is that of the control group. The result shows that the cells recovered after cryopreserved by the serum-free freezing medium of the present invention has higher cell viability and better adherence effect.

Example 8

Identification of the Surface Markers of the Stem Cells

The cells treated with the freezing medium of the present invention (of which the formula was described in Example 3) and the cells of control group were recovered respectively. The stem cells were centrifuged, resuspended, and counted. The concentrate of the cells was then adjusted to $1 \times 10^8$/L and centrifuged for 5 min. The supernatant was removed and the cells were washed with 4° C. cold D-Hanks and resuspended. The cell suspension was centrifuged at 800 r/min for 5 min again. The supernatant was removed, resuspended with D-Hanks to 1 mL, 5-10 μl of antibody was then added and kept out of light on ice for 30 min. Then it was washed with D-Hanks and the supernatant removed. Same wash protocol was repeated for 2-3 times to ensure that the uncombined antibodies were thoroughly washed away followed by adding about 200 to 300 μL of D-Hanks to form a suspension for the sorting by the Flow Cytometer. The antibodies added were antibodies against human CD34, CD45, CD29, CD73, CD90 and CD105, respectively.

The results were shown in FIG. 2. FIG. 2A is the flow cytometry map of CD34 monoclonal antibody, wherein the content of CD34 is 0%; FIG. 2B is the flow cytometry map of CD45 monoclonal antibody, wherein the content of CD45 is 0%; FIG. 2C is the flow cytometry map of CD29 monoclonal antibody, wherein the content of CD29 is 98.9%; FIG. 2D is the flow cytometry map of CD73 monoclonal antibody, wherein the content of CD73 is 93.5%; FIG. 2E is the flow cytometry map of CD90 monoclonal antibody, wherein the content of CD90 is 96.3%; FIG. 2F is the flow cytometry map of CD105 monoclonal antibody, wherein the content of CD34 is 73.3%.

Antigenic analysis result is shown in Table 3.

TABLE 3

| Surface antigen | CD34 | CD45 | CD29 | CD73 | CD90 | CD105 |
|---|---|---|---|---|---|---|
| Result | 0% | 0% | 98.9% | 93.5% | 96.3% | 73.3% |

Conclusion: The analysis of cell surface antigen marker was conducted after the adipose-derived stem cells were recovered after cryopreserved with serum-free freezing medium of the present invention. The result showed that the stem cells processed from the above-mentioned methods had higher purity, of which mainly were adipose-derived mesenchymal stem cells. For example, 98.9% of cells have CD29 surface antigen (which was a well-recognized adipose stem cell-specific antigen), but not CD34 antigen (a typical hematopoietic stem cell surface antigen), no cell has (0%) CD45 antigen (which was a known typical antigen located on the surface of leukocyte), either.

Example 9

Adipogenesis and Testing of Adipose-Derived Stem Cells

The freezing medium of the present invention (Example 3) was used to establish the cell bank of human adipose-derived stem cells. The stem cells were inoculated in 6-well plate with $2 \times 10^5$ cells per well after recovery. Stem cells in normal culture medium as negative control.

Methods of culture and induction: Final concentration of 1 μmol/L of dexamethasone, 10 umol/L of insulin, 200 umol/L of indomethacin and 0.5 mmol/L of isobutyl methylxanthine were added to the basic medium (DMEM+10% fetal calf serum) such as to prepared into the adipogenic medium. Cultural medium was changed twice a week until the adipogenic staining was performed. Parallel experiments for each group were also conducted (n=3).

Methods of Oil Red O Staining:

Staining: the nutrient solution was gently and gradually removed followed by gently washing with D-hanks. 10% neutral formalin was added and cytomembrane was fixed for 30 min. 0.5% Oil Red O was added (1.5 ml in 6-well plate) for staining for 10 min-1 h.

Bleaching, 75% ethanol/60% isopropanol used to rinse off the residual stain, re-staining with pale hematoxylin for 1 min followed by rinsing with PBS, mounted with glycerol gelatin, and observed with microscope.

5-10 views were randomly selected in each group of samples for observation by photographing to evaluate the adipogenic differentiation effect of the co-culturing method. The adipose is bright red, the cell nucleus blue, and the mesenchyme colorless.

The result shows that the adipose-derived stem cells cultured with the serum-free freezing medium of the present invention still have the ability to differentiate into fat cells when treated with adipogenesis inducer (FIG. 3). It can be seen in FIG. 3A that there are a large number of small lipid droplets clusters (red) in the adipogenic differentiated cells. FIG. 3B is the negative control, which are the stem cells without the treatment of differentiation inducer.

Example 10

Comparison of the Cryopreservation Effect of Different Types of Serum-Free Freezing Medium (Serum Substitute)

In order to evaluate the effect of the serum-free freezing medium of the present invention, the inventor used another serum-free freezing medium (serum substitute) for comparison: commercially available FetalClone III(SH30109.01) from HyClone company.

Serum-free freezing medium of the present invention: 10% of serum-free medium+12% DMSO+78% KSR (by volume)

Serum-free freezing medium of control group: 10% serum-free medium+12% DMSO+78% FetalClone III (by volume)

The third generation cells cryopreserved for a month were taken, and the number of viable cells was counted according to the method described in Example 5 after recovery.

The result is shown in Table 4.

TABLE 4

| Groups | Serum-free freezing medium of the present invention | Serum-free freezing medium of control group | Freezing medium containing serum of control group |
| --- | --- | --- | --- |
| 1 | 95.5% | 90.5% | 91.5% |
| 2 | 93.0% | 91.0% | 92.9% |
| 3 | 94.5% | 89.2% | 90.0% |
| 4 | 95.0% | 89.5% | 91.5% |
| 5 | 95.5% | 88.0% | 91.8% |
| Average | 94.7% | 89.6% | 91.5% |

The results from the test unexpectedly show that the effect of the recovery effect of the cells treated with the serum-free freezing medium of the present invention that does not contain any serum is the best, superior to that of the control groups treated by other serum-free freezing medium or the freezing medium containing serum.

This showed that, although most of the serum replacements were not suitable as alternatives of serum in freezing medium, the serum-free freezing medium containing KSR of the present invention has better effect in cryopreservation effect than that of serum-containing freezing medium. So the serum-free freezing medium of the present invention is ideal for the cryopreservation of adipose-derived stem cells.

Example 11

Comparison of the Effect of Cell Cryopreservation Using Serum-Free Freezing Medium with Different Formula Serum-free freezing mediums of four different formulas of the present invention were tested in this example, wherein the formulas were shown in Table 5.

The cell bank was prepared according to the method described in Example 3. After 3 months of cryopreservation, the adipose-derived stem cells from the bank were recovered according to the method described in Example 4. The cell viability was determined by the method described in Example 5.

TABLE 5

| Groups | Formula (by volume) |
| --- | --- |
| 1 | 7% serum-free medium + 8% DMSO + 85% KSR |
| 2 | 10% serum-free medium + 12% DMSO + 78% KSR |
| 3 | 15% serum-free medium + 15% DMSO + 70% KSR |
| 4 | 5% serum-free medium + 15% DMSO + 80% KSR |

The result shows that the adipose-derived stem cells from banks established with the four different formulas of the present invention all have high survival rates (about 93-95%) after recovery.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A serum-free freezing medium comprising the following ingredients: serum-free culture medium, dimethylsulfoxide (DMSO), and serum substitute KSR,
   wherein the freezing medium does not contain any serum; and relative to the volume of serum-free freezing medium, the serum-free culture medium makes up a proportion of a in a range from 5%-15% (v/v), the DMSO makes up a proportion of b in a range from 8%-20% (v/v), and the KSR makes up a proportion of c in a range from 70%-85% (v/v), where a+b+c≤100%.

2. The serum-free freezing medium of claim 1, wherein a is in a range from 8%-12% (v/v), b is in a range from 10%-14% (v/v), and c is in a range from 75%-80% (v/v) by volume.

3. A method for long-term storing of an adipose-derived stem cell and/or establishing an adipose-derived stem cell library comprising:
   mixing the adipose-derived stem cell with the serum-free freezing medium of claim 1 to form a mixture.

* * * * *